United States Patent
Toothman

(10) Patent No.: US 10,039,805 B1
(45) Date of Patent: *Aug. 7, 2018

(54) INFANT FORMULAS HAVING VITAMIN COMPLEXES WITH ENHANCED BIOAVAILABILITY

(71) Applicant: Michelle Ann Toothman, Alexandria, VA (US)

(72) Inventor: Michelle Ann Toothman, Alexandria, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/054,833

(22) Filed: Feb. 26, 2016

(51) Int. Cl.
| | |
|---|---|
| *A61K 38/17* | (2006.01) |
| *A61K 31/70* | (2006.01) |
| *A61K 31/201* | (2006.01) |
| *A61K 31/675* | (2006.01) |
| *A61K 31/519* | (2006.01) |
| *A61K 31/714* | (2006.01) |
| *A61K 33/06* | (2006.01) |
| *A61K 33/34* | (2006.01) |
| *A61K 33/26* | (2006.01) |
| *A61K 33/32* | (2006.01) |
| *A61K 33/00* | (2006.01) |
| *A61K 33/04* | (2006.01) |
| *A61K 33/30* | (2006.01) |
| *A61K 31/375* | (2006.01) |
| *A61K 31/14* | (2006.01) |
| *A61K 31/4188* | (2006.01) |
| *A61K 31/525* | (2006.01) |
| *A61K 31/51* | (2006.01) |
| *A61K 31/197* | (2006.01) |
| *A61K 31/07* | (2006.01) |
| *A61K 31/355* | (2006.01) |
| *A61K 31/122* | (2006.01) |
| *A61K 31/202* | (2006.01) |
| *A23C 9/152* | (2006.01) |
| *A23C 9/158* | (2006.01) |

(52) U.S. Cl.
CPC .......... *A61K 38/1709* (2013.01); *A23C 9/158* (2013.01); *A23C 9/1526* (2013.01); *A61K 31/07* (2013.01); *A61K 31/122* (2013.01); *A61K 31/14* (2013.01); *A61K 31/197* (2013.01); *A61K 31/201* (2013.01); *A61K 31/202* (2013.01); *A61K 31/355* (2013.01); *A61K 31/375* (2013.01); *A61K 31/4188* (2013.01); *A61K 31/51* (2013.01); *A61K 31/519* (2013.01); *A61K 31/525* (2013.01); *A61K 31/675* (2013.01); *A61K 31/70* (2013.01); *A61K 31/714* (2013.01); *A61K 33/00* (2013.01); *A61K 33/04* (2013.01); *A61K 33/06* (2013.01); *A61K 33/26* (2013.01); *A61K 33/30* (2013.01); *A61K 33/32* (2013.01); *A61K 33/34* (2013.01)

(58) Field of Classification Search
CPC .... A61K 31/519; A61K 31/047; A61K 31/07; A61K 31/122; A61K 31/14; A61K 31/197; A61K 31/355; A61K 31/375; A61K 31/4188; A61K 31/201; A61K 31/675; A61K 31/51; A61K 31/525; A61K 31/593; A61K 31/714; A61K 31/70; A61K 33/04; A61K 33/06; A61K 33/00; A61K 33/26; A61K 33/34; A61K 33/30; A61K 33/32

See application file for complete search history.

(56) References Cited

U.S. PATENT DOCUMENTS

| | | |
|---|---|---|
| 5,686,491 A | 11/1997 | Sherwood |
| 6,190,724 B1 | 2/2001 | Sawatzki et al. |
| 6,365,177 B1 | 4/2002 | Shahadeh |
| 6,589,576 B2 | 7/2003 | Borschel et al. |
| 6,613,367 B1 * | 9/2003 | Wells ................. A61K 31/4415 426/590 |
| 6,645,543 B2 | 11/2003 | Gohman et al. |
| 6,777,391 B1 | 8/2004 | Kratky et al. |
| 6,863,918 B2 | 3/2005 | Bindels et al. |
| 6,913,778 B2 * | 7/2005 | Kuhlman ............. A23C 9/1512 426/583 |
| 7,070,825 B2 | 7/2006 | Ndife et al. |
| 8,377,430 B2 * | 2/2013 | Donnet-Hughes ... A61K 35/741 424/93.1 |
| 2008/0145475 A1 | 6/2008 | Flatt et al. |
| 2010/0068346 A1 | 3/2010 | Hodges |
| 2014/0323574 A1 | 10/2014 | Yao et al. |
| 2015/0140174 A1 | 5/2015 | Shao et al. |
| 2015/0335052 A1 * | 11/2015 | Sprenger ................. A23L 1/296 426/61 |

FOREIGN PATENT DOCUMENTS

WO    WO 2013/138906 A1 * 9/2013

OTHER PUBLICATIONS

Greenberg et al. ("Folic Acid Supplementation and Pregnancy: More Than Just Neural Tube Defect Prevention" in Reviews in Obstetrics and Gynecology, vol. 4, 2011).*

* cited by examiner

*Primary Examiner* — Blessing M Fubara
(74) *Attorney, Agent, or Firm* — King & Partners, PLC

(57) ABSTRACT

An infant food formulation having a vitamin complex with enhanced bioavailability, including a protein; a carbohydrate; a fat; and a vitamin B complex, wherein the vitamin B complex includes a vitamer of vitamin $B_6$, a vitamer of vitamin $B_9$, and a vitamer of vitamin $B_{12}$.

11 Claims, No Drawings

INFANT FORMULAS HAVING VITAMIN COMPLEXES WITH ENHANCED BIOAVAILABILITY

CROSS-REFERENCE TO RELATED APPLICATIONS

Not Applicable.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to infant formulas and, more particularly, to novel, infant formulas that comprise vitamin complexes having enhanced bioavailability for maximizing nutritional absorption. While the infant formulas of the present invention are suitable for a broad range of infants, they are particularly beneficial for infants that, for example, present genetic (e.g., known or unknown MTHFR CT polymorphism) or other types of disorders. The infant formulas of the present invention are preferably suitable for use in powder, liquid concentrate, and liquid ready-to-feed forms.

2. Background Art

Infant formulas have been known in the art for years and are the subject of a plurality of patents and/or publications, including: U.S. Pat. No. 8,377,430 entitled "Infant Formula with Probiotics," U.S. Pat. No. 7,070,825 entitled "Infant Formula," U.S. Pat. No. 6,913,778 entitled "Infant Formula Compositions Comprising Increased Amounts of Alpha-Lactalbumin," U.S. Pat. No. 6,863,918 entitled "Infant Formula with Improved Protein Content," U.S. Pat. No. 6,777,391 entitled "Composition for an Infant Formula Having a Low Threonine Content," U.S. Pat. No. 6,645,543 entitled "Infant Formula with Free Amino Acids and Nucleotides," U.S. Pat. No. 6,613,367 entitled "Infant Formula," U.S. Pat. No. 6,589,576 entitled "Pediatric Formula and Methods for Providing Nutrition and Improving Tolerance," U.S. Pat. No. 6,365,177 entitled "Insulin Supplemented Infant Formula," U.S. Pat. No. 6,190,724 entitled "Infant Formula," U.S. Pat. No. 5,686,491 entitled "Infant Formula," United States Patent Application Publication No. 2015/0335052 entitled "Oligosaccharide Mixture and Food Product Comprising this Mixture, Especially Infant Formula," United States Patent Application Publication No. 2015/0140174 entitled "Infant Formula Milk Powder and Preparation Method Thereof," United States Patent Application Publication No. 2014/0323574 entitled "Infant Formula with High SN-2 Palmitate and Oligofructose," United States Patent Application Publication No. 2010/0068346 entitled "Infant Formula," and United States Patent Application Publication No. 2008/0145475 entitled "Use of DPA(n-6) Oils in Infant Formula," all of which are hereby incorporated herein by reference in their entirety—including all references cited therein.

U.S. Pat. No. 8,377,430 appears to disclose an infant formula comprising a source of protein in an amount of not more than 2.0 g/100 kcal, a source of lipids, a source of carbohydrate and a probiotic wherein the probiotic is present in an amount equivalent to between $10^2$ and $10^5$ cfu/g of dry formula. The invention further extends to the use of such an infant formula to modulate the immune system of a neonatal infant to promote the development in the first few weeks of the life of the infant of a beneficial intestinal microbiota comparable with that found in breast fed babies as well as to promote the maturation of the immune system of a neonatal infant in the first few weeks of life.

U.S. Pat. No. 7,070,825 appears to disclose a new unit dose packaging for infant formula. The infant formula is manufactured as a tablet. One tablet will typically contain sufficient nutrients to produce a single serving of the formula (i.e., the amount of formula an average infant consumes in a single feeding). Other aspects of the invention are directed to feeding an infant such a reconstituted tablet and packaging containing such infant formula tablets.

U.S. Pat. No. 6,913,778 appears to disclose an infant formula composition comprising a whey fraction wherein 40% or less of the total protein in said fraction is alpha-lactalbumin and more than 8% of the total protein in said whey fraction is beta-lactoglobulin, with the proviso that the percentage of alpha-lactalbumin in said whey fraction is greater than the percentage of beta-lactoglobulin in said whey fraction.

U.S. Pat. No. 6,863,918 appears to disclose an improved infant formula resulting in reduced constipation, abdominal discomfort and gastrointestinal problems, that comprises at least one protein component having a phosphorus content of less than 0.75 g P/100 g protein, and at least one lipid component that can be easily digested by an infant. Preferably, it further comprises at least one prebiotic component, and at least one viscosity-improving component. The protein fraction of the formula is preferably a hydrolysate prepared by hydrolysing a protein starting material, especially a whey protein with a combination of an endoproteinase and an exoproteinase.

U.S. Pat. No. 6,777,391 appears to disclose a composition for an infant formula which comprises a low threonine content; a method of producing the composition; use of the composition in the manufacture of a medicament or nutritional product for addressing the nutritional needs and providing healthy growth of an infant; and a method of addressing the nutritional needs and providing healthy growth of an infant which comprises administering an effective amount of the composition. A preferred embodiment of the composition comprises all of: i) acid whey protein or sweet whey protein from which caseino-glycomacropeptide has been removed; and ii) free arginine; and iii) free histidine; and iv) free tyrosine or free tryptophan or tryptophan rich milk protein or a mixture thereof.

U.S. Pat. No. 6,645,543 appears to disclose a fat-rich powder that provides the complete nutritional needs of an at-risk infant no more than one year old, who has acquired a milk allergy, such as cow's milk allergy ("CMA"), and/or an allergy to protein in "soy milk", as well as digestive or absorption problems resulting in a damaged gut. Because such an infant must derive all its protein from amino acids it is not fed any ingredient derived from mammalian milk, but a combination of amino acids with nucleotides in specified amounts along with free L-glutamine, maintaining specified ratios of their relative amounts, which ratios in the ranges stated are found to be beneficial for healing of the infant's damaged gut, and for promoting cell division to assure its normal growth. A typical feeding of 32.6 gm of the powder delivers 160 cals; the powder, including triglycerides of relatively long chain fatty acids which contribute about 50% of the total caloric content of the powder, is nevertheless solubilized when the powder is manually shaken at 35 degrees Centigrade in a bottle containing 240 ml (8 fl oz) of water.

U.S. Pat. No. 6,613,367 appears to disclose products for complete nutrition of infants. The products are characterized by the type and amount of protein and carbohydrate and the increased levels of folic acid, vitamin B6 and vitamin B12 or their functional equivalents. These products improve feelings of well-being of infants, especially those of young age, and are useful in the treatment and prevention of diseases that are associated with disorders of serotonin- and melatonin metabolism.

U.S. Pat. No. 6,589,576 appears to disclose an improved pediatric formula and methods for providing nutrition to and enhancing tolerance in pediatric patients. The formula may be provided in powder, concentrate or ready-to-feed forms. The pediatric formula comprises, based on a 100 kcal basis, about 8 to about 16 grams carbohydrate (preferably about 9.4 to about 12.3 grams), about 3 to about 6 grams lipid (preferably about 4.7 to about 5.6 grams), about 1.8 to about 3.3 grams protein (preferably about 2.4 to about 3.3 grams), and a tolerance improver comprising a sufficient quantity for xanthum gum to produce a viscosity of no greater than about 200 centipoise at a pH of 4.0, or less. The formula may also be provided in a powder. The formula preferably further comprises vitamins and minerals and may further comprise a stabilizer. The methods comprise administering to a pediatric patient an effective amount of a pediatric formula according to the invention, as described above.

U.S. Pat. No. 6,365,177 appears to disclose an infant formula in a powder or solution form including nutritional components and an insulin supplement. A method of feeding an infant including the steps of dissolving an infant formula powder containing nutritional components and an insulin supplement in water for obtaining a solution including said nutritional components and said insulin supplement and feeding the infant with the solution.

U.S. Pat. No. 6,190,724 appears to disclose a protein composition and a baby food (e.g., infant formula). The protein composition is characterized in that it contains at least 15 wt % (based on the total amount of the proteins) modified proteins, the course of whose digestion is slowed compared to the unmodified, normal proteins serving as starting materials. Such a protein composition and a baby food containing this create just as good metabolic conditions for the normal development of a child as feeding with human milk proteins.

U.S. Pat. No. 5,686,491 appears to disclose an infant formula for infants with metabolic disorders in fatty acid catabolism such as medium-chain acyl-CoA dehydrogenase deficiency (MCAD), long-chain acyl-CoA dehydrogenase deficiency (LOAD), short-chain acyl-CoA dehydrogenase deficiency (SCAD), multiple acyl-CoA dehydrogenase deficiency (MADD), Sudden Infant Death Syndrome (SIDS) and failure to thrive syndrome. The present invention also provides an assay for diagnosing children and infants with metabolic disorders such as failure to thrive syndrome; a method for treating failure to thrive syndrome; and a process for normalizing the lipid content of the mitochondrial membrane. In particular, the present invention provides an infant formula containing 90-130 cals/Kg which comprises (a) 2.5-3.5 g/Kg protein; (b) carbohydrate; (c) fat; and (d) ≥500 mg carnitine, wherein the ratio of carbohydrate to fat is greater than or equal to 60:40.

United States Patent Application Publication No. 2015/0335052 appears to disclose an oligosaccharide mixture comprising 5-70 wt % of at least one N-acetylated oligosaccharide, 5-90 wt % of at least one neutral oligosaccharide, 2-50 wt % of at least one sialylated oligosaccharide, and/or 5-70 wt % of at least one fucosylated oligosaccharide. The invention also discloses a food product, especially an infant formula, comprising said oligosaccharide mixture.

United States Patent Application Publication No. 2015/0140174 appears to disclose an infant formula milk powder capable of preventing and alleviating infant iron deficiency anemia and a preparation method thereof. The formula milk powder comprises components such as vegetable oil, fresh milk, whey powder, lactose powder, whey protein powder, oligosaccharides, complex vitamins and complex minerals, wherein the lactoferrin and vitamin C, or alternatively, an iron source (calculated as iron), lactoferrin and vitamin C are maintained in the appropriate mass ratios, and the formula milk powder of the present invention is obtained by performing mixing, homogenizing, cooling, concentrating and spray-drying, packaging or directly using a step-by-step mixing method. The formula milk powder comprises appropriate amounts of vitamin C and lactoferrin, as well as an appropriate amount of iron source as further provided, and the three are combined according to an appropriate proportion, so that the combination of the three kinds of the substances have a synergistic effect, and the absorption and utilization rate of iron are increased dramatically, thereby not only achieving the desirable iron supplementation effect, but also preventing and alleviating the phenomenon of infant iron deficiency anemia.

United States Patent Application Publication No. 2014/0323574 appears to disclose an infant formula having a relatively high content of triglycerides having palmitic acid in the sn-2 position. The formula may include oligofructose. The formula may also include at least one omega 6 fatty acid and at least one omega 3 fatty acid. The formula may also have a relatively low protein content and an alpha-lactalbumin content similar to human milk. The invention also includes a method for improving the stool consistency, increasing bifidobacteria in the colon, reducing potentially pathogenic bacteria in the colon and reducing calcium soaps in the stool of a formula-fed infant.

United States Patent Application Publication No. 2010/0068346 appears to disclose an infant formula which is cow's milk, hydroisolate, rice, goat's milk and/or soy based. The infant formula may be processed such that its manganese concentration is lower than an average manganese concentration associated with the infant formula base. Further, the infant formula may be fortified with iron (lactoferrin), calcium, vitamin D and omega 3 fatty acids to help maintain a neonate's manganese absorption rate at a normal or otherwise acceptable level.

United States Patent Application Publication No. 2008/0145475 appears to disclose infant formula compositions containing docosapentaenoic acid n-6 ("DPA(n-6)") and other polyunsaturated fatty acids and methods for their preparation and use are provided.

While the infant formulas disclosed supra have been known in the art for years, issues associated with ingredient absorption, bioavailability, safety, and shelf life remain largely problematic and/or unsolved. As such, there is a genuine demand for novel infant formulas that comprise vitamin complexes having enhanced bioavailability for maximizing nutritional absorption.

These and other objects of the present invention will become apparent in light of the present specification, claims, chemical structures, chemical formulae, and drawings.

SUMMARY OF THE INVENTION

The present invention is directed to an infant food formulation having a vitamin complex with enhanced bioavailability, comprising, consisting essentially of, and/or consisting of: (a) a protein; (b) a carbohydrate; (c) a fat; and (d) a vitamin B complex, wherein the vitamin B complex comprises: (1) a first vitamin, wherein the first vitamin comprises a form of vitamin $B_6$; (2) a second vitamin, wherein the second vitamin comprises folate or a form of vitamin $B_9$; and (3) a third vitamin, wherein the third vitamin comprises a form of vitamin $B_{12}$.

In a preferred embodiment of the present invention, the first vitamin comprises the structure of formula I or nutraceutically acceptable salts or solvates thereof:

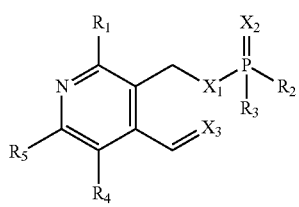

(I)

wherein $R_1$-$R_6$, are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s); wherein at least three of $R_1$-$R_5$ comprise OH; and wherein $X_1$-$X_3$ are each independently selected from the group consisting of N—$R_6$; O; and S.

In another preferred embodiment of the present invention, the first vitamin comprises the structure of formula II or nutraceutically acceptable salts or solvates thereof:

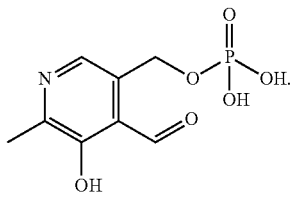

(II)

In yet another preferred embodiment of the present invention, the second vitamin comprises the structure of formula III or nutraceutically acceptable salts or solvates thereof:

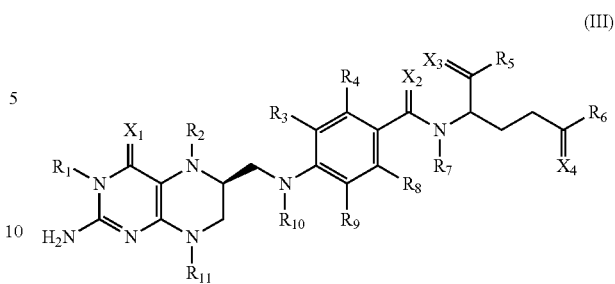

(III)

wherein $R_1$-$R_{12}$, are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s); and wherein $X_1$-$X_4$ are each independently selected from the group consisting of N—$R_{12}$; O; and S.

In another aspect of the present invention, the second vitamin comprises the structure of formula IV or nutraceutically acceptable salts or solvates thereof:

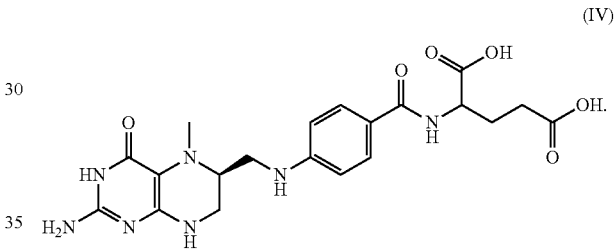

(IV)

In a preferred embodiment of the present invention, the third vitamin comprises the structure of formula V or nutraceutically acceptable salts or solvates thereof:

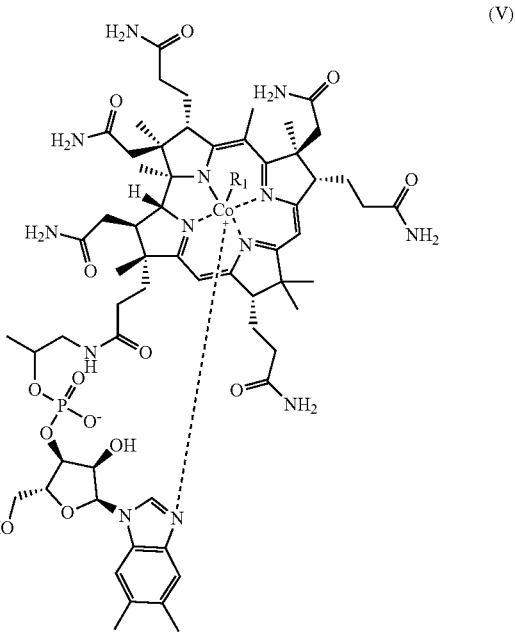

(V)

wherein $R_1$ is selected from the group consisting of an alkyl, cycloalkyl, polycycloalkyl, heterocycloalkyl, aryl, alkaryl, aralkyl, alkoxy, alkanoyl, aroyl, alkenyl, alkylalkenyl, alcohol, ether, ketone, carboxylic acid, acid halide, acid anhydride, ester, and/or amide group containing approximately 1 to approximately 25 carbon atom(s).

In another preferred embodiment of the present invention, the third vitamin comprises the structure of formula VI or nutraceutically acceptable salts or solvates thereof:

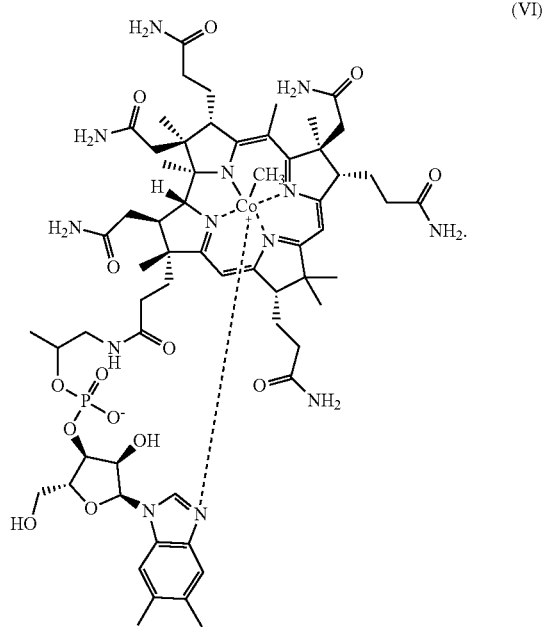

(VI)

Preferably, the first vitamin comprises [(4-formyl-5-hydroxy-6-methylpyridin-3-yl)methoxy]phosphonic acid, the second vitamin comprises (4-((((S)-2-amino-5-methyl-4-oxo-3,4,5,6,7,8-hexahydropteridin-6-yl)methyl)amino) benzoyl) glutamic acid, and the third vitamin comprises methylcobalamin.

In one embodiment of the present invention, the weight ratio of the first vitamin to the second vitamin to the third vitamin ranges from approximately 250:75:1 to approximately 100:25:1 by weight of the total infant food formulation, and more preferably is approximately 200:55:1 by weight of the total infant food formulation.

In a preferred embodiment of the present invention, the protein comprises at least one of animal protein and plant protein. In this embodiment the protein comprises, for example, egg protein, milk protein, whey protein, whey protein concentrate, whey protein isolate, whey protein hydrolysate, casein protein, hydrolyzed protein, soy protein, rice protein, and/or pea protein.

In another preferred embodiment of the present invention, the carbohydrate comprises a starch, a complex carbohydrate, a sugar, a simple carbohydrate, and/or a fiber.

In yet another preferred embodiment of the present invention, the fat comprises a saturated fat, a trans fat, a monounsaturated fat, and/or a polyunsaturated fat. In this embodiment the fat preferably comprises hexadecatrienoic acid (HTA), α-linolenic acid (ALA), stearidonic acid (SDA), eicosatrienoic acid (ETE), eicosatetraenoic acid (ETA), eicosapentaenoic acid (EPA), heneicosapentaenoic acid (HPA), docosapentaenoic acid (DPA), clupanodonic acid, docosahexaenoic acid (DHA), tetracosapentaenoic acid, tetracosahexaenoic acid (Nisinic acid), linolenic acid (LA), gamma-linolenic acid (GLA), calendic acid, eicosadienoic acid, dihomo-gamma-linolenic acid (DGLA), arachidonic acid (AA), docosadienoic acid, adrenic acid, docosapentaenoic acid, tetracosatetraenoic acid, and/or tetracosapentaenoic acid.

Additional examples of suitable fats for use in accordance with the present invention comprise octanoic acid, dodecanoic acid, lauric acid derived from, for example, coconut oil, myristic acid derived from, for example, coconut oil, hexadecanoic acid, palmitic acid derived from, for example, palm oil, adrenic acid, octadecanoic acid, and fatty acids derived from sunflower seeds, safflower seeds, soya beans, and/or olives.

In a preferred embodiment of the present invention, the infant food formulation comprises one or more amino acids, including, but not limited to, L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and/or L-valine.

In another preferred embodiment of the present invention, the infant food formulation comprises one or more vitamins and/or minerals. In this embodiment, the vitamins and/or minerals, preferably include vitamin A, thiamin, riboflavin, niacin, pantothenic acid, biotin, vitamin C, choline, vitamin D, vitamin E, vitamin K, calcium, chloride, chromium, copper, fluoride, iodine, iron, magnesium, manganese, molybdenum, nickel, phosphorus, potassium, silicon, selenium, sodium, sulfur, tin, vanadium, and/or zinc.

The present invention is also directed to an infant food formulation having a vitamin complex with enhanced bioavailability, comprising, consisting essentially of, and/or consisting of: (a) a protein; (b) a carbohydrate; (c) a fat; (d) a vitamin B complex, wherein the vitamin B complex comprises: (1) a first vitamin, wherein the first vitamin comprises [(4-formyl-5-hydroxy-6-methylpyridin-3-yl)methoxy]phosphonic acid; (2) a second vitamin, wherein the second vitamin comprises (4-((((S)-2-amino-5-methyl-4-oxo-3,4,5,6,7,8-hexahydropteridin-6-yl)methyl)amino)benzoyl) glutamic acid; and (3) a third vitamin, wherein the third vitamin comprises methylcobalamin, wherein the weight ratio of the first vitamin to the second vitamin to the third vitamin ranges from approximately 250:75:1 to approximately 100:25:1 by weight of the total infant food formulation; and (e) at least five amino acids selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine.

The present invention is yet further directed to an infant food formulation having a vitamin complex with enhanced bioavailability, consisting of: (a) a protein; (b) a carbohydrate; (c) a fat; (d) a vitamin B complex, wherein the vitamin B complex comprises: (1) a first vitamin, wherein the first vitamin comprises [(4-formyl-5-hydroxy-6-methylpyridin-3-yl)methoxy]phosphonic acid; (2) a second vitamin, wherein the second vitamin comprises (4-((((S)-2-amino-5-methyl-4-oxo-3,4,5,6,7,8-hexahydropteridin-6-yl)methyl)amino)benzoyl) glutamic acid; and (3) a third vitamin, wherein the third vitamin comprises methylcobalamin, wherein the weight ratio of the first vitamin to the second vitamin to the third vitamin ranges from approximately 250:75:1 to approximately 100:25:1 by weight of the total infant food formulation; (e) an amino acid; (f) vitamins other than B vitamins; (g) minerals; and (h) wherein any remainder comprises adjunct agents.

DETAILED DESCRIPTION OF THE INVENTION

While this invention is susceptible of embodiment in many different forms, there is shown in the structural formulas and described herein in detail several specific embodiments with the understanding that the present disclosure is to be considered as an exemplification of the principles of the invention and is not intended to limit the invention to the embodiments illustrated. It will be understood that the structural formulas disclosed herein are intended to comprise all stereochemcial configurations regardless of graphical representations.

In accordance with the present invention, infant formulas are disclosed herein that include vitamins and/or vitamin complexes having enhanced bioavailability for maximizing nutritional absorption. Without being bound by any one particular theory, it is believed that the infant formulas of the present invention facilitate enhanced bioavailability by reducing and/or eliminating multi-step biochemical conversions and/or are formulated in such a manner that relevant vitamins or their nutraceutically acceptable salts or solvates are neither compromised and/or adversely affected by other and/or adjunct ingredients. It will be understood that the infant formulas of the present invention are suitable for use in powder (e.g., non-compressed, partially compressed, compressed, etcetera), liquid concentrate, and liquid ready-to-feed forms.

In a first embodiment of the present invention, the infant food formulation preferably includes a protein, a carbohydrate, a fat, and a vitamin complex having enhanced bioavailability for maximizing nutritional absorption, relative to infant food formulations having primarily synthetic vitamers. In accordance with the present invention the vitamin complex preferably includes a first vitamin, wherein the first vitamin comprises a specific vitamer of vitamin $B_6$, a second vitamin, wherein the second vitamin comprises a specific vitamer of vitamin $B_9$, and a third vitamin, wherein the third vitamin comprises a specific vitamer of vitamin $B_{12}$.

For purposes of the present disclosure, the first vitamin preferably comprises the structure of formula I or nutraceutically acceptable salts (e.g., deprotonated derivatives) or solvates thereof:

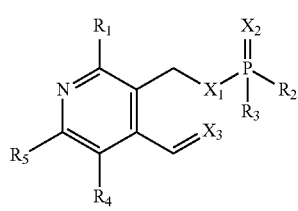

(I)

wherein $R_1$-$R_6$, are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s); wherein at least three of $R_1$-$R_5$ comprise OH; and wherein $X_1$-$X_3$ are each independently selected from the group consisting of N—$R_6$; O; and S. In particular, the first vitamin preferably comprises the structure of formula II or nutraceutically acceptable salts or solvates thereof:

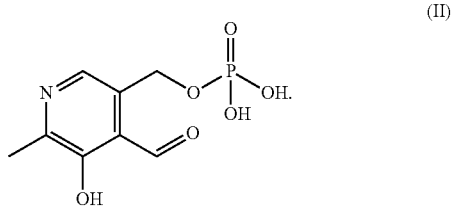 [SMILES: Cc1ncc(COP(=O)(O)O)c(C=O)c1O]

(II)

For purposes of reducing any potential ambiguity associated with the structure of formula II, it will be understood that this structure is a vitamer of vitamin $B_6$ known as [(4-formyl-5-hydroxy-6-methylpyridin-3-yl)methoxy]phosphonic acid and/or pyridoxal-5'-phosphate and is commercially available from Sigma-Aldrich—among other chemical suppliers.

In one embodiment, the second vitamin preferably comprises a folate derivative and/or the structure of formula III or nutraceutically acceptable salts or solvates thereof:

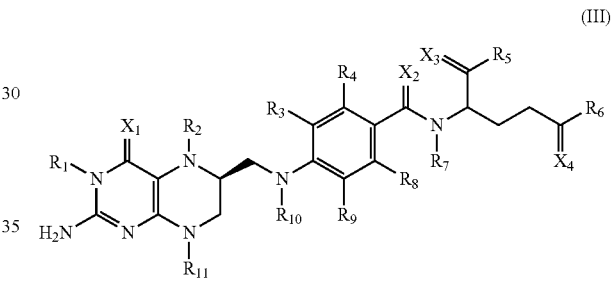

(III)

wherein $R_1$-$R_{12}$, are each independently selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkyl-alkenyl, alcohol, ether, ketone, carboxylic acid, acid halide, acid anhydride, ester, and/or amide group containing approximately 1 to approximately 25 carbon atom(s); and wherein $X_1$-$X_4$ are each independently selected from the group consisting of N—$R_{12}$; O; and S. In particular, the second vitamin preferably comprises the structure of formula IV or nutraceutically acceptable salts or solvates thereof:

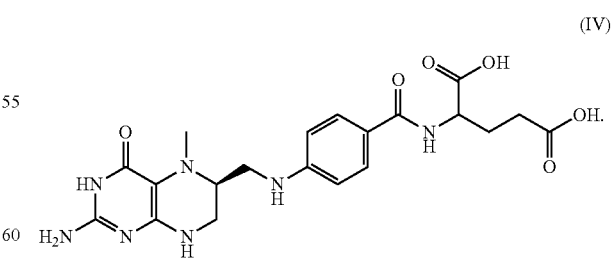

(IV)

For purposes of reducing any potential ambiguity associated with the structure of formula IV, it will be understood that this structure is a vitamer of vitamin $B_9$ known as (6S)-5-methyltetrahydrofolate and is commercially available from Parchem—among other chemical suppliers.

In accordance with the present invention, the third vitamin preferably comprises the structure of formula V or nutraceutically acceptable salts or solvates thereof:

(V)

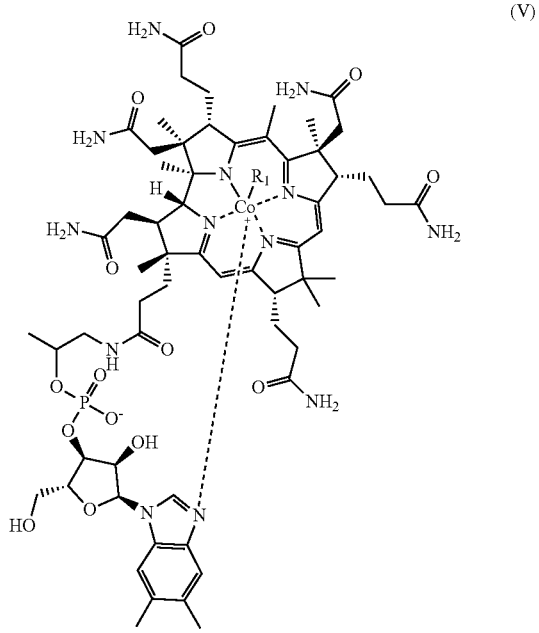

wherein $R_1$ is selected from the group consisting of H; OH; and an alkyl, cycloalkyl, polycycloalkyl, heterocycloalkyl, aryl, alkaryl, aralkyl, alkoxy, alkanoyl, aroyl, alkenyl, alkylalkenyl, alcohol, ether, ketone, carboxylic acid, acid halide, acid anhydride, ester, and/or amide group containing approximately 1 to approximately 25 carbon atom(s). In particular, the third vitamin preferably comprises the structure of formula V or nutraceutically acceptable salts or solvates thereof:

(VI)

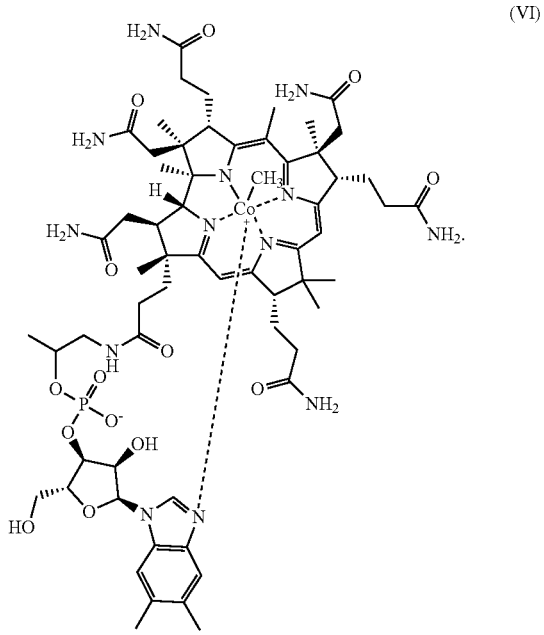

For purposes of reducing any potential ambiguity associated with the structure of formula VI, it will be understood that this structure is a vitamer of vitamin $B_{12}$ known as methylcobalamin and is commercially available from Sigma-Aldrich—among other chemical suppliers.

The weight ratio of the first vitamin to the second vitamin to the third vitamin preferably ranges from approximately 300:100:1 to approximately 100:20:1 by weight of the total infant food formulation, and more preferably ranges from approximately 250:75:1 to approximately 100:25:1 by weight of the total infant food formulation. In one embodiment, the weight ratio of the first vitamin to the second vitamin to the third vitamin is approximately 200:55:1 by weight of the total infant food formulation.

Preferably the infant food formulations of the present invention include animal protein and/or plant protein. Suitable examples of proteins include, for example, egg protein, milk protein, whey protein, whey protein concentrate, whey protein isolate, whey protein hydrolysate, casein protein, hydrolyzed protein, soy protein, rice protein, and/or pea protein.

The infant food formulations of the present invention, preferably include one or more carbohydrates, such as, but not limited to, a starch, a complex carbohydrate, a sugar, a simple carbohydrate, and/or a fiber. It will be understood that the weight ratio of the first vitamin to the second vitamin and the third vitamin to the carbohydrate preferably ranges from approximately 200,000:1 to approximately 100,000:1 by weight of the total infant food formulation, and more preferably ranges from approximately 175,000:1 to approximately 130,000:1 by weight of the total infant food formulation.

In accordance with the present invention, the fat preferably comprises a saturated fat, a trans fat, a monounsaturated fat, and/or a polyunsaturated fat—especially including omega-3 and omega-6 fatty acids. Suitable examples include, but are not limited to, hexadecatrienoic acid, α-linolenic acid, stearidonic acid, eicosatrienoic acid, eicosatetraenoic acid, eicosapentaenoic acid, heneicosapentaenoic acid, docosapentaenoic acid, clupanodonic acid, docosahexaenoic acid, tetracosapentaenoic acid, tetracosahexaenoic acid, linoleic acid, gamma-linolenic acid, calendic acid, eicosadienoic acid, dihomo-gamma-linolenic acid, arachidonic acid, docosadienoic acid, adrenic acid, docosapentaenoic acid, tetracosatetraenoic acid, and/or tetracosapentaenoic acid.

The infant food formulations of the present invention also preferably includes one or more amino acids. Non-limiting examples of amino acids include L and D enantiomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and/or valine.

In one embodiment of the present invention, the infant food formulations also preferably include one or more prebiotics, such as galacto- and fructo-oligosaccharides, also known as oligogalactosyllactose, oligogalactose, oligolactose or trans galactooligosaccharides (TOS).

Preferably, the infant food formulations also include one or more nucleotides (adenosine-5'-monophosphate, cytidine-5'-monophosphate, disodium guanosine-5'-monophosphate, disodium uridine-5'-monophosphate, etcetera).

Preferably, the infant food formulations of the present invention include additional vitamins and minerals. Examples include vitamin A, other B vitamins, thiamin, riboflavin, niacin, pantothenic acid, biotin, vitamin C, choline, vitamin D, vitamin E, vitamin K, calcium, chloride, chromium, copper, fluoride, iodine, iron (e.g., ferrous gluconate, Ferronyl™) magnesium, manganese, molybdenum, nickel, phosphorus, potassium, silicon, selenium, sodium, sulfur, tin, vanadium, zinc, and combinations thereof.

In a preferred embodiment of the present invention, the infant food formulations further comprise adjunct agents including, but not limited to, preservatives, anti-microbial agents, oral hygiene additives, medicaments, herbal additives, additional anti-oxidants, emulsifying agents, buffers, sweeteners, lactoferrin and related derivatives, scents, colorants, flavorants, viscosity modifiers, thickening agents, stabilizers, and/or a solvents (e.g., water, milk, etcetera) to dissolve any solutes.

Provided below is a non-limiting example of an infant formula in accordance with the present invention. The vitamins and minerals to be included are as follows and are specified for each 100 kilocalories of the infant formula in the form prepared for consumption as directed on the container: Vitamin A (250-750 IU), Vitamin D (40-100 IU), Vitamin E (minimum 0.7 IU), Vitamin K (minimum 4 mcg), Thiamine-Vitamin B1 (minimum 40 mcg), Riboflavin-Vitamin B2 (minimum 60 mcg), Pyridoxal-5-phosphate-Vitamin B6 (minimum 35 mcg), Methylcobalamin-Vitamin B12 (minimum 0.15 mcg), Niacin (minimum 250 mcg), Folate (minimum 4 mcg), Pantothenic acid (minimum 300 mcg), Biotin (required for non-milk-based formula only, minimum 1.5 mcg), Vitamin C (minimum 8 mg), Choline (required for non-milk-based formula only, minimum 7 mg), Inositol (required for non-milk-based formula only, minimum 4 mg), Calcium (minimum 60 mg), Phosphorus (minimum 30 mg), Magnesium (minimum 6 mg), Iron (0.15-3.0 mg), Zinc (minimum 0.5 mg), Manganese (minimum 5 mcg), Copper (minimum 60 mcg), Iodine (5-75 mcg), Selenium (2-7 mcg), Sodium (20-60 mg), Potassium (80-200 mg), Chloride (55-150 mg). The infant formula compositions may also further comprise suitable types of lipid, carbohydrates, and protein as will be recognized by those skilled in the art. The amount of lipid or fat can vary from about 3 to about 7 g/100 kcal. The amount of protein can vary from about 1 to about 5 g/100 kcal. The amount of carbohydrate can vary from about 8 to about 12 g/100 kcal.

Provided below are non-limiting examples of infant food formulations. Ingredients are provided per 100 kcal.

Example 1

| Ingredient Name | Amount | Source |
|---|---|---|
| Nonfat milk | .1-10 g | Marroquin Organic |
| Carbohydrates (e.g., corn syrup solids, lactose, glucose syrup solids, sugar) | 1-50 g | Grain Millers, Marroquin Organic |
| Fat (e.g., high oleic sunflower oil, high oleic safflower oil, soy oil, coconut oil, palm oil or palm olein) | 0.1-200 g | Connoils |
| Soy or Sunflower lecithin | 5-500 mg | American Lecithin |
| Whey protein concentrate | .1-50 g | Grain Millers |
| Mixed tocopherol concentrate or natural mixed tocopherols | 1-500 ppm | Organic Technologies |
| Calcium (e.g., calcium carbonate, calcium citrate malate, calcium citrate, calcium phosphate, calcium ascorbate, calcium chloride, calcium hydroxide) | 10-500 mg | Parchem |
| Copper (e.g., cupric sulfate, copper citrate, copper gluconate) | 5-200 mcg | Parchem |
| Iron (e.g., ferrous sulfate, ferrous fumarate, ferrous gluconate, Ferronyl™ carbonyl iron) | .5-5.0 mg | Parchem/Ashland |
| Magnesium (e.g., magnesium oxide, magnesium citrate, magnesium chloride, magnesium glycinate, magnesium phosphate) | 1-50 mg | Parchem |
| Manganese (e.g., manganese sulfate, manganese citrate, manganese gluconate) | 1-50 mcg | Parchem |
| Potassium iodide | 5-500 mcg | Parchem |
| Potassium (e.g., potassium bicarbonate, potassium chloride, potassium phosphate, potassium hydroxide, potassium citrate) | 1-450 mg | Parchem |
| Selenium (e.g., sodium selenite, l-selenomethionine, sodium selenate) | 1-50 mcg | Parchem |
| Zinc (e.g., zinc sulfate, zinc picolinate, zinc gluconate, zinc citrate, zinc acetate) | .5-50 mg | Parchem |
| Vitamin C (e.g., ascorbic acid, sodium ascorbate, calcium ascorbate) | 1-500 mg | Parchem |
| Sodium (e.g., sodium chloride, sodium citrate) | 2-200 mg | Parchem |
| Choline (e.g., choline chloride, choline bitartrate, choline citrate) | 1-200 mg | Parchem |
| Biotin | .5-20 mcg | Parchem |
| Inositol | 1-100 mg | Parchem |
| Taurine | 1-100 mg | Parchem |
| (6S-5-methyltetrahydrofolate glucosamine salt | 1-100 mcg | Gnosis |
| Methylcobalamin | 0.10-5.0 mcg | Parchem |
| Pyridoxal-5-Phosphate | 5-350 mcg | Parchem |
| Riboflavin (e.g., Riboflavin, Riboflavin-5-Phosphate) | 5-500 mcg | Parchem |
| Thiamine (e.g., thiamine hydrochloride, thiamine mononitrate) | 1-100 mcg | Parchem |
| Calcium pantothenate | 100-700 mcg | Parchem |
| Niacinamide | 25-1,000 mcg | Parchem |
| Vitamin A (e.g., beta carotene, Vitamin A Palmitate) | 25-1,000 IU | Parchem |
| Cholecalciferol | 25-1,000 IU | Parchem |
| Vitamin E (e.g., dl-alpha tocopheryl acetate, d-alpha tocopherol acetate, d-alpha tocopherol succinate) | 0.1-20 IU | Parchem |
| Vitamin K (e.g., Phytonadione, Phylloquinone) | 1-20 mcg | Parchem |

Example 2

| Ingredient Name | Amount | Source |
|---|---|---|
| Nonfat milk | .1-10 g | Marroquin Organic |
| Carbohydrates (e.g., corn syrup solids, lactose, glucose syrup solids, sugar) | 1-50 g | Grain Millers, Marroquin Organic |
| Fat (e.g., high oleic sunflower oil, high oleic safflower oil, soy oil, coconut oil, palm oil or palm olein) | 0.1-200 g | Connoils |
| Soy or Sunflower lecithin | 5-500 mg | American Lecithin |
| Whey protein concentrate | .1-50 g | Grain Millers |
| Mixed tocopherol concentrate or natural mixed tocopherols | 1-500 ppm | Organic Technologies |
| Calcium (e.g., calcium carbonate, calcium citrate malate, calcium citrate, calcium phosphate, calcium ascorbate, calcium chloride, calcium hydroxide) | 10-500 mg | Parchem |
| Copper (e.g., cupric sulfate, copper citrate, copper gluconate) | 5-200 mcg | Parchem |
| Iron (e.g., ferrous sulfate, ferrous fumarate, ferrous gluconate, Ferronyl™ carbonyl iron) | .5-5.0 mg | Parchem/Ashland |
| Magnesium (e.g., magnesium oxide, magnesium citrate, magnesium chloride, magnesium glycinate, magnesium phosphate) | 1-50 mg | Parchem |
| Manganese (e.g., manganese sulfate, manganese citrate, manganese gluconate) | 1-50 mcg | Parchem |
| Potassium iodide | 5-500 mcg | Parchem |
| Vitamin C (e.g., ascorbic acid, sodium ascorbate, calcium ascorbate | 1-500 mg | Parchem |
| Sodium (e.g., sodium chloride, sodium citrate) | 2-200 mg | Parchem |
| Choline (e.g., choline chloride, choline bitartrate, choline citrate) | 1-200 mg | Parchem |
| Taurine | 1-100 mg | Parchem |
| (6S)-5-methyltetrahydrofolate glucosamine salt | 1-100 mcg | Gnosis |
| Methylcobalamin | 0.10-5.0 mcg | Parchem |
| Pyridoxal-5-Phosphate | 5-350 mcg | Parchem |
| Calcium pantothenate | 100-700 mcg | Parchem |
| Niacinamide | 25-1,000 mcg | Parchem |
| Vitamin A (e.g., beta carotene, Vitamin A Palmitate) | 25-1,000 IU | Parchem |
| Cholecalciferol | 25-1,000 IU | Parchem |
| Vitamin E (e.g., dl-alpha tocopheryl acetate, d-alpha tocopherol acetate, d-alpha tocopherol succinate) | 0.1-20 IU | Parchem |
| Vitamin K (e.g., Phytonadione, Phylloquinone) | 1-20 mcg | Parchem |

Example 3

| Ingredient Name | Amount | Source |
|---|---|---|
| Nonfat milk | .1-10 g | Marroquin Organic |
| Carbohydrates (e.g., corn syrup solids, lactose, glucose syrup solids, sugar) | 1-50 g | Grain Millers, Marroquin Organic |
| Fat (e.g., high oleic sunflower oil, high oleic safflower oil, soy oil, coconut oil, palm oil or palm olein) | 0.1-200 g | Connoils |
| Soy or Sunflower lecithin | 5-500 mg | American Lecithin |
| Whey protein concentrate | .1-50 g | Grain Millers |
| Mixed tocopherol concentrate or natural mixed tocopherols | 1-500 ppm | Organic Technologies |
| Calcium (e.g., calcium carbonate, calcium citrate malate, calcium citrate, calcium phosphate, calcium ascorbate, calcium chloride, calcium hydroxide) | 10-500 mg | Parchem |
| Copper (e.g., cupric sulfate, copper citrate, copper gluconate) | 5-200 mcg | Parchem |
| Iron (e.g., ferrous sulfate, ferrous fumarate, ferrous gluconate, Ferronyl™ carbonyl iron) | .5-5.0 mg | Parchem/Ashland |
| Magnesium (e.g., magnesium oxide, magnesium citrate, magnesium chloride, magnesium glycinate, magnesium phosphate) | 1-50 mg | Parchem |
| Manganese (e.g., manganese sulfate, manganese citrate, manganese gluconate) | 1-50 mcg | Parchem |
| Potassium iodide | 5-500 mcg | Parchem |
| Potassium (e.g., potassium bicarbonate, potassium chloride, potassium phosphate, potassium hydroxide, potassium citrate) | 1-450 mg | Parchem |
| Selenium (e.g., sodium selenite, I-selenomethionine, sodium selenate) | 1-50 mcg | Parchem |
| Zinc (e.g., zinc sulfate, zinc picolinate, zinc gluconate, zinc citrate, zinc acetate) | .5-50 mg | Parchem |
| Vitamin C (e.g., ascorbic acid, sodium ascorbate, calcium ascorbate | 1-500 mg | Parchem |
| Sodium (e.g., sodium chloride, sodium citrate) | 2-200 mg | Parchem |
| Choline (e.g., choline chloride, choline bitartrate, choline citrate) | 1-200 mg | Parchem |
| Biotin | .5-20 mcg | Parchem |
| Inositol | 1-100 mg | Parchem |
| Taurine | 1-100 mg | Parchem |

| Ingredient Name | Amount | | Source |
| --- | --- | --- | --- |
| (6S)-5-methyltetrahydrofolate glucosamine salt | 1-100 | mcg | Gnosis |
| Methylcobalamin | 0.10-5.0 | mcg | Parchem |
| Pyridoxal-5-Phosphate | 5-350 | mcg | Parchem |

Example 4

| Ingredient Name | Amount | | Source |
| --- | --- | --- | --- |
| Nonfat milk | .5-4 | g | Marroquin Organic |
| Carbohydrates (e.g., corn syrup solids, lactose, glucose syrup solids, sugar) | 1-25 | g | Grain Millers, Marroquin Organic |
| Fat (e.g., high oleic sunflower oil, high oleic safflower oil, soy oil, coconut oil, palm oil or palm olein) | 0.5-20 | g | Connoils |
| Soy or Sunflower lecithin | 50-300 | mg | American Lecithin |
| Whey protein concentrate | .5-4 | g | Grain Millers |
| Mixed tocopherol concentrate or natural mixed tocopherols | 1-300 | ppm | Organic Technologies |
| Calcium (e.g., calcium carbonate, calcium citrate malate, calcium citrate, calcium phosphate, calcium ascorbate, calcium chloride, calcium hydroxide) | 60-100 | mg | Parchem |
| Copper (e.g., cupric sulfate, copper citrate, copper gluconate) | 60-90 | mcg | Parchem |
| Iron (e.g., ferrous sulfate, ferrous fumarate, ferrous gluconate, Ferronyl ™ carbonyl iron) | .5-3.0 | mg | Parchem/Ashland |
| Magnesium (e.g., magnesium oxide, magnesium citrate, magnesium chloride, magnesium glycinate, magnesium phosphate) | 6-40 | mg | Parchem |
| Manganese (e.g., manganese sulfate, manganese citrate, manganese gluconate) | 5-25 | mcg | Parchem |
| Potassium iodide | 15-30 | mcg | Parchem |
| Potassium (e.g., potassium bicarbonate, potassium chloride, potassium phosphate, potassium hydroxide, potassium citrate) | 8-300 | mg | Parchem |
| Selenium (e.g., sodium selenite, I-selenomethionine, sodium selenate) | 2-7 | mcg | Parchem |
| Zinc (e.g., zinc sulfate, zinc picolinate, zinc gluconate, zinc citrate, zinc acetate) | .5-2 | mg | Parchem |
| Vitamin C (e.g., ascorbic acid, sodium ascorbate, calcium ascorbate) | 10-20 | mg | Parchem |
| Sodium (e.g., sodium chloride, sodium citrate) | 20-60 | mg | Parchem |
| Choline (e.g., choline chloride, choline bitartrate, choline citrate) | 5-35 | mg | Parchem |
| Biotin | 1.5-6 | mcg | Parchem |
| Inositol | 4-8 | mg | Parchem |
| Taurine | 5-12 | mg | Parchem |
| (6S)-5-methyltetrahydrofolate glucosamine salt | 4-30 | mcg | Gnosis |
| Methylcobalamin | 0.15-0.7 | mcg | Parchem |
| Pyridoxal-5-Phosphate | 35-80 | mcg | Parchem |
| Riboflavin (e.g., Riboflavin, Riboflavin-5-Phosphate) | 60-175 | mcg | Parchem |
| Thiamine (e.g., thiamine hydrochloride, thiamine mononitrate) | 40-100 | mcg | Parchem |
| Calcium pantothenate | 300-500 | mcg | Parchem |
| Niacinamide | 250-1100 | mcg | Parchem |
| Vitamin A (e.g., beta carotene, Vitamin A Palmitate) | 250-500 | IU | Parchem |
| Cholecalciferol | 40-100 | IU | Parchem |
| Vitamin E (e.g., dl-alpha tocopheryl acetate, d-alpha tocopherol acetate, d-alpha tocopherol succinate) | 0.7-5 | IU | Parchem |
| Vitamin K (e.g., Phytonadione, Phylloquinone) | 4-10 | mcg | Parchem |

Example 5

| Ingredient Name | Amount | | Source |
| --- | --- | --- | --- |
| Nonfat milk | 2-4 | g | Marroquin Organic |
| Carbohydrates (e.g., corn syrup solids, lactose, glucose syrup solids, sugar) | 5-25 | g | Grain Millers, Marroquin Organic |
| Fat (e.g., high oleic sunflower oil, high oleic safflower oil, soy oil, coconut oil, palm oil or palm olein) | 5-20 | g | Connoils |
| Soy or Sunflower lecithin | 50-100 | mg | American Lecithin |
| Whey protein concentrate | 1-4 | g | Grain Millers |
| Mixed tocopherol concentrate or natural mixed tocopherols | 1-100 | ppm | Organic Technologies |
| Calcium (e.g., calcium carbonate, calcium citrate malate, calcium citrate, calcium phosphate, calcium ascorbate, calcium chloride, calcium hydroxide) | 50-100 | mg | Parchem |

-continued

| Ingredient Name | Amount | Source |
|---|---|---|
| Copper (e.g., cupric sulfate, copper citrate, copper gluconate) | 50-100 mcg | Parchem |
| Iron (e.g., ferrous sulfate, ferrous fumarate, ferrous gluconate, Ferronyl ™ carbonyl iron) | 1-2.0 mg | Parchem/Ashland |
| Magnesium (e.g., magnesium oxide, magnesium citrate, magnesium chloride, magnesium glycinate, magnesium phosphate) | 10-25 mg | Parchem |
| Manganese (e.g., manganese sulfate, manganese citrate, manganese gluconate) | 10-25 mcg | Parchem |
| Potassium iodide | 15-30 mcg | Parchem |
| Potassium (e.g., potassium bicarbonate, potassium chloride, potassium phosphate, potassium hydroxide, potassium citrate) | 10-50 mg | Parchem |
| Selenium (e.g., sodium selenite, l-selenomethionine, sodium selenate) | 5-10 mcg | Parchem |
| Zinc (e.g., zinc sulfate, zinc picolinate, zinc gluconate, zinc citrate, zinc acetate) | 1-5 mg | Parchem |
| Vitamin C (e.g., ascorbic acid, sodium ascorbate, calcium ascorbate | 10-20 mg | Parchem |
| Sodium (e.g., sodium chloride, sodium citrate) | 20-50 mg | Parchem |
| Choline (e.g., choline chloride, choline bitartrate, choline citrate) | 10-30 mg | Parchem |
| Biotin | 1-5 mcg | Parchem |
| Inositol | 1-5 mg | Parchem |
| Taurine | 5-10 mg | Parchem |
| (6S)-5-methyltetrahydrofolate glucosamine salt | 5-25 mcg | Gnosis |
| Methylcobalamin | 0.15-0.5 mcg | Parchem |
| Pyridoxal-5-Phosphate | 5-50 mcg | Parchem |
| Riboflavin (e.g., Riboflavin, Riboflavin-5-Phosphate) | 25-75 mcg | Parchem |
| Thiamine (e.g., thiamine hydrochloride, thiamine mononitrate) | 20-80 mcg | Parchem |
| Calcium pantothenate | 50-100 mcg | Parchem |
| Niacinamide | 25-500 mcg | Parchem |
| Vitamin A (e.g., beta carotene, Vitamin A Palmitate) | 50-300 IU | Parchem |
| Cholecalciferol | 20-75 IU | Parchem |
| Vitamin E (e.g., dl-alpha tocopheryl acetate, d-alpha tocopherol acetate, d-alpha tocopherol succinate) | 0.5-2 IU | Parchem |
| Vitamin K (e.g., Phytonadione, Phylloquinone) | 2-5 mcg | Parchem |

Example 6

| Ingredient Name | Amount | Source |
|---|---|---|
| Nonfat milk | .5-4 g | Marroquin Organic |
| Carbohydrates (e.g., corn syrup solids, lactose, glucose syrup solids, sugar) | 1-25 g | Grain Millers, Marroquin Organic |
| Fat (e.g., high oleic sunflower oil, high oleic safflower oil, soy oil, coconut oil, palm oil or palm olein) | 0.5-20 g | Connoils |
| Whey protein concentrate | .5-4 g | Grain Millers |
| (6S)-5-methyltetrahydrofolate glucosamine salt | 4-30 mcg | Gnosis |
| Methylcobalamin | 0.15-0.7 mcg | Parchem |
| Pyridoxal-5-Phosphate | 35-80 mcg | Parchem |

Example 7

| Ingredient Name | Amount | Source |
|---|---|---|
| Carbohydrates (e.g., corn syrup solids, lactose, glucose syrup solids, sugar) | 5-20 g | Grain Millers, Marroquin Organic |
| Fat (e.g., high oleic sunflower oil, high oleic safflower oil, soy oil, coconut oil, palm oil or palm olein) | 0.5-10 g | Connoils |
| Whey protein concentrate | .5-5 g | Grain Millers |
| (6S)-5-methyltetrahydrofolate glucosamine salt | 4-25 mcg | Gnosis |
| Methylcobalamin | 0.15-0.5 mcg | Parchem |
| Pyridoxal-5-Phosphate | 40-60 mcg | Parchem |

It will be further understood that any reference to compounds disclosed herein includes salts and/or solvates of the same.

The infant formulas of the present invention are intended for infants up to 12 months of age, but could also include variations that are called toddler and "follow up" formulas and are labeled as such.

The foregoing description merely explains and illustrates the invention and the invention is not limited thereto except insofar as the appended claims are so limited, as those skilled in the art who have the disclosure before them will be able to make modifications without departing from the scope of the invention.

What is claimed and desired to be secured by Letters Patent of the United States is:

1. An infant food formulation having a vitamin complex with enhanced bioavailability, comprising:
   a protein;
   a carbohydrate;
   a fat; and
   a vitamin B complex, wherein the vitamin B complex comprises:
      a first vitamin, wherein the first vitamin comprises [(4-formyl-5-hydroxy-6-methylpyridin-3-yl)methoxy]phosphonic acid;
      a second vitamin, wherein the second vitamin comprises N-[4-[[[(6S)-2-amino-1,4,5,6,7,8-hexahydro-5-methyl-4-oxo-6-pteridinyl]methyl]amino]benzoyl]-L-glutamic acid, glucosamine salt; and
      a third vitamin, wherein the third vitamin comprises methylcobalamin, wherein the weight ratio of the first vitamin to the second vitamin to the third vitamin ranges from approximately 250:75:1 to approximately 100:25:1 by weight of the total infant food formulation.

2. The infant food formulation according to claim 1, wherein the weight ratio of the first vitamin to the second vitamin to the third vitamin is approximately 200:55:1 by weight of the total infant food formulation.

3. The infant food formulation according to claim 1, comprising a caloric density of approximately 20 to approximately 30 kcal/fluid ounce.

4. The infant food formulation according to claim 1, wherein the protein comprises at least one of egg protein, milk protein, whey protein, whey protein concentrate, whey protein isolate, whey protein hydrolysate, casein protein, hydrolyzed protein, soy protein, rice protein, and pea protein.

5. The infant food formulation according to claim 1, wherein the carbohydrate comprises at least one of a starch, a complex carbohydrate, a sugar, a simple carbohydrate, and a fiber.

6. The infant food formulation according to claim 1, wherein the fat comprises at least one of a saturated fat, a trans fat, a monounsaturated fat, and a polyunsaturated fat.

7. The infant food formulation according to claim 1, wherein the fat comprises at least one of hexadecatrienoic acid, α-linolenic acid, stearidonic acid, eicosatrienoic acid, eicosatetraenoic acid, eicosapentaenoic acid, heneicosapentaenoic acid, docosapentaenoic acid, clupanodonic acid, docosahexaenoic acid, tetracosapentaenoic acid, and tetracosahexaenoic acid.

8. The infant food formulation according to claim 1, wherein the fat comprises at least one of linoleic acid, gamma-linolenic acid, calendic acid, eicosadienoic acid, dihomo-gamma-linolenic acid, arachidonic acid, docosadienoic acid, adrenic acid, docosapentaenoic acid, tetracosatetraenoic acid, and tetracosapentaenoic acid.

9. The infant food formulation according to claim 1, further comprising an amino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, L-valine, and combinations thereof.

10. The infant food formulation according to claim 1, further comprising a vitamin/mineral selected from the group consisting of vitamin A, thiamin, riboflavin, niacin, pantothenic acid, biotin, vitamin C, choline, vitamin D, vitamin E, vitamin K, calcium, chloride, chromium, copper, fluoride, iodine, iron, magnesium, manganese, molybdenum, nickel, phosphorus, potassium, silicon, selenium, sodium, sulfur, tin, vanadium, zinc, and combinations thereof.

11. An infant food formulation having a vitamin complex with enhanced bioavailability, consisting of:
   from 0.5 g to 4 g of nonfat milk per 100 kcal of the infant food formulation;
   from 1 g to 25 g collectively of lactose and glucose syrup solids per 100 kcal of the infant food formulation;
   from 0.5 g to 20 g collectively of high oleic sunflower oil and high oleic safflower oil per 100 kcal of the infant food formulation;
   from 50 mg to 300 mg of sunflower lecithin per 100 kcal of the infant food formulation;
   from 0.5 g to 4 g of whey protein concentrate per 100 kcal of the infant food formulation;
   from 1 ppm to 300 ppm of natural mixed tocopherols per 100 kcal of the infant food formulation;
   from 60 mg to 100 mg of calcium citrate malate per 100 kcal of the infant food formulation;
   from 60 mcg to 90 mcg of copper citrate per 100 kcal of the infant food formulation;
   from 0.5 mg to 3.0 mg of ferrous fumarate per 100 kcal of the infant food formulation;
   from 6 mg to 40 mg of magnesium chloride per 100 kcal of the infant food formulation;
   from 5 mcg to 25 mcg of manganese citrate per 100 kcal of the infant food formulation;
   from 15 mcg to 30 mcg of potassium iodide per 100 kcal of the infant food formulation;
   from 8 mg to 300 mg of potassium citrate per 100 kcal of the infant food formulation;
   from 2 mcg to 7 mcg of L-selenomethionine per 100 kcal of the infant food formulation;
   from 0.5 mg to 2 mg of zinc picolinate per 100 kcal of the infant food formulation;
   from 10 mg to 20 mg of sodium ascorbate per 100 kcal of the infant food formulation;
   from 20 mg to 60 mg of sodium citrate per 100 kcal of the infant food formulation;
   from 5 mg to 35 mg of choline bitartrate per 100 kcal of the infant food formulation;
   from 1.5 mcg to 6 mcg of biotin per 100 kcal of the infant food formulation;
   from 4 mg to 8 mg of inositol per 100 kcal of the infant food formulation;
   from 5 mg to 12 mg of taurine per 100 kcal of the infant food formulation;
   from 4 mcg to 30 mcg of N-[4-[[[(6S)-2-amino-1,4,5,6,7,8-hexahydro-5-methyl-4-oxo-6-pteridinyl]methyl]amino]benzoyl]-L-glutamic acid, glucosamine salt per 100 kcal of the infant food formulation;
   from 0.15 mcg to 0.7 mcg of methylcobalamin per 100 kcal of the infant food formulation;
   from 35 mcg to 80 mcg of [(4-formyl-5-hydroxy-6-methylpyridin-3-yl)methoxy]phosphonic acid per 100 kcal of the infant food formulation;
   from 60 mcg to 175 mcg of riboflavin-5-phosphate per 100 kcal of the infant food formulation;
   from 40 mcg to 100 mcg of thiamine mononitrate per 100 kcal of the infant food formulation;
   from 300 mcg to 500 mcg of calcium pantothenate per 100 kcal of the infant food formulation;
   from 250 mcg to 1,100 mcg of niacinamide per 100 kcal of the infant food formulation;

from 250 IU to 500 IU of vitamin A palmitate per 100 kcal of the infant food formulation;

from 40 IU to 100 IU of cholecalciferol per 100 kcal of the infant food formulation;

from 0.7 IU to 5 IU of D-alpha tocopherol acetate per 100 kcal of the infant food formulation; and from 4 mcg to 10 mcg of phylloquinone per 100 kcal of the infant food formulation.

\* \* \* \* \*